United States Patent [19]
Frick et al.

[11] Patent Number: 6,004,938
[45] Date of Patent: Dec. 21, 1999

[54] INOSITOLGLYCANS HAVING INSULIN-LIKE ACTION

[75] Inventors: Wendelin Frick, Huenstetten-Beuerbach; Guenter Mueller, Sulzbach, both of Germany

[73] Assignee: Hoescht Aktiengesellschaft, Frankfurt, Germany

[21] Appl. No.: 08/979,865

[22] Filed: Nov. 26, 1997

[30] Foreign Application Priority Data

Nov. 28, 1996 [DE] Germany .............................. 196 49 350

[51] Int. Cl.$^6$ .............................. A01N 43/04; A61K 38/28
[52] U.S. Cl. ..................................... 514/25; 514/3; 514/4; 514/7; 514/8; 514/53; 514/54; 514/62; 514/866; 536/4.1; 536/17.2; 536/17.5; 536/18.5; 536/55.1; 536/123.1; 536/123.13
[58] Field of Search .................................. 514/3, 4, 7, 8, 514/25, 53, 54, 62, 866; 536/17.2, 17.5, 4.1, 18.5, 55.1, 123.1, 123.13

[56] References Cited

U.S. PATENT DOCUMENTS

| | | |
|---|---|---|
| 4,446,064 | 5/1984 | Larner et al. . |
| 4,906,468 | 3/1990 | Saltiel . |
| 5,624,903 | 4/1997 | Müller et al. . |
| 5,652,221 | 7/1997 | Larner et al. . |

FOREIGN PATENT DOCUMENTS

| | | |
|---|---|---|
| 0 132 769 | 2/1985 | European Pat. Off. . |
| 0 132 770 | 2/1985 | European Pat. Off. . |
| 0 532 915 | 3/1993 | European Pat. Off. . |
| 0 545 198 | 6/1993 | European Pat. Off. . |
| 96/14075 | 5/1996 | WIPO . |
| WO 96/14075 | 5/1996 | WIPO . |

OTHER PUBLICATIONS

Chemical Abstracts, Columbus, Ohio, vol. 123, No. 7 (IGGS) (1995), abstract of T. Muragata et al., "Preparation of Physiologically Active Inositol Glycans.", Jap. 06 293790, p. 1105.

Zapata et al., Building blocks for the synthesis of glycosyl–myo–inositols involved in the insulin intracellular signalling process, *Carbohydr. Res.* 234 (1992), pp. 93–106.

Murakata, Chikara et al., Synthetic Study on Glycophosphatidyl Inositol (GPI) Anchor of Trypanosoma Brucei: Glycoheptaosyl Core$^1$, *Tetrahedron Ltrs.*, vol. 31, No. 17, pp. 2439–2442, 1990.

Elie, C.J.J., et al., "Synthesis of 6–O–(a–D–Mannopyranosy)–D–myo–inositol: A Fragment From Mycobacteria Phospholipids", vol. 46, No. 24, pp. 8243–8254, 1990.

Termin, Andrea, et al., "6–O–Benzylierte Muraminsaeure als Glycosylakzeptor—Synthese des GlcNAc–β(1→4)–MurNAc–Disaccharids", *Liebigs Ann. Chem.*, pp. 789–795, 1989.

Mayer, Thomas G., et al., "Synthese eines GPI–Ankers der Hefe (*Saccharomyces cerevisiae*)★★", Angew. Chem., vol. 106, No. 21, pp. 2289–2293, 1994.

Bannwarth, Willi, et al., "A Simple and Effective Chemical Phosphorylation Procedure for Biomolecules", *Helvetica Chimica Acta*, vol. 70, pp. 175–186, 1987.

Aneja, Rajindra, et al., "The Absolute Configuration and Optical Purity of (–) and (+) –1,2:4,5–Di–Ocyclohexylidene–myo–inositols", *Tetrahedron: Asymmetry*, vol. 6, No. 1, pp. 17–18, 1995.

*Primary Examiner*—James O. Wilson
*Attorney, Agent, or Firm*—Foley & Lardner

[57] ABSTRACT

The invention relates to inositolglycans having insulin-like action. Specific compounds are provided having the formula I $$A—Z—R \qquad (I)$$

where A is the radical H—P(O)(OH)—, H—P(S)(OH)—, HO—P(S)(OH)—, HS—P(S)(OH)—, $(C_1-C_4)$-alkyl-P(O)(OH)—, $(C_1-C_4)$-alkyl-P(S)(OH)—, $S(O)_2(OR^1)$—, $S(O)(OR^1)$—, $NH_2$—C(O)—, $R^1R^2N$—, $R^1R^2N$—C(O)—NH—, $R^1O$—$SO_2$—NH—, $(C_1-C_4)$-alkyl-$SO_2$—, $(C_1-C_4)$-alkyl-S(O)— or $R^1$—S—, Z is 2 to 6 substituted or unsubstituted sugar radicals and R is substituted or unsubstituted inositol. The inventive compounds are suitable for the treatment of diabetes mellitus or noninsulin-dependent diabetes.

10 Claims, No Drawings

INOSITOLGLYCANS HAVING INSULIN-LIKE ACTION

BACKGROUND OF THE INVENTION

The invention relates to inositolglycans having insulin-like action, which are suitable for the treatment of diabetes mellitus.

It is known that the metabolic action of insulin also causes the formation of low molecular weight compounds which also have insulin-like action (U.S. Pat. No. 4,446,064). A number of inositolglycan compounds have already been proposed which have insulin-like action (WO 96/14075, JP 6/293790, JP 4/120089).

Diabetes type II, noninsulin-dependent diabetes, is accompanied by insulin resistance of the peripheral tissue, such as muscle or fatty tissue. The glucose utilization, which is thereby reduced, is caused by a lack of insulin stimulation of glucose transport and subsequent metabolic processes.

SUMMARY OF THE INVENTION

It is therefore an object of the invention to provide compounds having insulin-like action, exhibiting good serum stability, having insulin-like action on insulin-resistant tissues and suitability for the treatment of diabetes mellitus. According to this object of the invention, novel compounds are provided having the formula I

$$A\text{—}Z\text{—}R \quad (I)$$

where A is the radical H—P(O)(OH)—, H—P(S)(OH)—, HO—P(S)(OH)—, HS—P(S)(OH)—, $(C_1\text{-}C_4)$-alkyl-P(O)(OH)—, $(C_1\text{-}C_4)$-alkyl-P(S)(OH)—, $S(O)_2(OR^1)$—, $S(O)(OR^1)$—, $NH_2$—C(O)—, $R^1R^2N$—, $R^1R^2N$—C(O)—NH—, $R^1O$—$SO_2$—NH—, $(C_1\text{-}C_4)$-alkyl-$SO_2$—, $(C_1\text{-}C_4)$-alkyl-S(O)— or $R^1$—S—, Z is 2 to 6 substituted or unsubstituted sugar radicals and R is substituted or unsubstituted inositol.

According to this same object, pharmaceutical compositions are provided. In one embodiment pharmaceutical compositions comprise at least one compound having formula I and/or a physiologically tolerable salt thereof. In other embodiment, pharmaceutical compositions are provided which comprise at least one compound according to formula I and at least one member of the group consisting of modified insulin, unmodified insulin and an insulin derivative.

It is a further object of the invention to provide methods for synthesizing inositolglycan compounds which have insulin-like activity. According to this object of the invention, methods of synthesis are provided for preparing compounds of formula I.

It is yet another object of the invention to provide methods of treatment which utilize compounds having insulin-like activity. According to this object of the invention, methods of treatment are provided which comprise administering to a patient in need of treatment an efficacious amount of a compound according to formula I. According to one embodiment, the patient is suffering from diabetes mellitus or noninsulin-dependent diabetes.

DETAILED DESCRIPTION OF THE INVENTION

Compounds of the Invention

The invention therefore relates to inositolglycans having insulin-like action, of the formula I

$$A\text{—}Z\text{—}R \quad (I)$$

and/or physiologically tolerable salts of the compound of the formula I and/or stereoisomeric forms of the compound of the formula I, where A is the radical
1) H—P(O)(OH)—,
2) H—P(S)(OH)—,
3) HO—P(S)(OH)—,
4) HS—P(S)(OH)—,
5) $(C_1\text{-}C_4)$-alkyl-P(O)(OH)—,
6) $(C_1\text{-}C_4)$-alkyl-P(S)(OH)—,
7) $S(O)_2(OR^1)$—,
8) $S(O)(OR^1)$—,
9) $NH_2$—C(O)—,
10) $R^1R^2N$—,
11) $R^1R^2N$—C(O)—NH—,
12) $R^1O$—$SO_2$—NH—,
13) $(C_1\text{-}C_4)$-alkyl-$SO_2$—,
14) $(C_1\text{-}C_4)$-alkyl-S(O)— or
15) $R^1$—S—
   in which $R^1$ and $R^2$ independently of one another are hydrogen or $(C_1\text{-}C_4)$-alkyl, Z is 1) 2 to 6 sugar radicals,
2) 2 to 6 sugar radicals, mono- to hexasubstituted independently of one another by
   2.1 methyl,
   2.2 sugar radical
   2.3 disugar radical
   2.4 —$SO_2$—OH,
   2.5 —C(O)—$NR^1R^2$,
   2.6 —C(O)—$(C_1\text{-}C_4)$-alkyl,
   2.7 —P(O)(H)OH,
   2.8 —$P(O)(OH)_2$,
   2.9 —P(S)(H)OH,
   2.10 —$P(S)(OH)_2$,
   2.11 —P(S)(SH)(OH),
   2.12 —P(O)(OH)—O—$CH_2$—$CH_2$—$NR^1R^2$ or
   2.13 the glycosidic bond between the 2 to 6 sugar radicals is
   replaced one to six times by —$CH_2$— or —S—, and
      in which $R^1$ and $R^2$ independently of one another are a hydrogen atom or $(C_1\text{-}C_4)$-alkyl, R is 1) inositol,
2) inositol phosphate,
3) inositol thiophosphate,
4) inositol cyclophosphate,
5) inositol cyclothiophosphate,
6) a radical from the group defined under R 2) to 5) mono- or disubstituted independently of one another by
   6.1 phosphate or
   6.2 thiophosphate,
7) a radical from the group defined under R 2) to 5) monosubstituted by
   7.1 a cyclophosphate radical or
   7.2 a cyclothiophosphate radical, or
8) inositol, where two adjacent OH groups are substituted by
   8.1 —$CH_2$—$SO_2$—NH—.

Preferred compounds of the formula I are those wherein
A is 1) H—P(O)(OH)—,
    2) $S(O)_2(OR^1)$— or
    3) $NH_2$—C(O)—

Z is 1) 2 to 6 sugar radicals which originate from the group consisting of
   1.1 mannose,
   1.2 glucose, 1.3 gluconic acid,
1.4 galactonic acid,
1.5 mannonic acid,
1.6 glucosamine,
1.7 fructose or
1.8 galactose,
2) 2 to 6 sugar radicals which originate from the group defined under Z1.1 to 1.8 and are mono- to hexasubstituted independently of one another by
2.1 methyl,
2.2 mannose,
2.3 glucosamine,
2.4 dimannose or
2.5 mannose-glucosamine and the glycosidic bond of the two sugars mannose and glucosamine is between the carbon atoms 1–3, 1–2 or 1–6 of the two sugars, and R is 1) inositol,
2) inositol phosphate,
3) inositol thiophosphate,
4) inositol cyclothiophosphate or
5) inositol cyclophosphate.

Particularly preferred compounds of the formula I are those wherein

A is H—P(O)(OH)—,

Z is 1) 2 to 4 sugar radicals which originate from the group consisting of
1.1 mannose or
1.2 glucosamine or
2) 2 to 4 sugar radicals which originate from the group consisting of
2.1 mannose or
2.2 glucosamine, monosubstituted by mannose and R is 1) inositol,
2) inositol phosphate or
3) inositol cyclophosphate.

Sugar radicals are understood as meaning compounds which are derived from aldoses and ketoses having 3 to 7 carbon atoms, which can belong to the D or L series; these also include amino sugars or uronic acids. Examples which may be mentioned are glucose, mannose, fructose, galactose, ribose, erythrose, glyceraldehyde, sedoheptulose, glucosamine, galactosamine, glucuronic acid, galacturonic acid, gluconic acid, galactonic acid or mannonic acid. By disugar, saccharides are meant which consist of two sugar units. Tri-, tetra-, penta- or hexasugars are formed by acetal-like linkage of 3 to 6 sugars. The linkages can in this case occur in the α- or β-form. The linkages between the sugars preferably take place via carbon atom 1 and carbon atom 6, carbon atom 1 and carbon atom 2, and carbon atom 1 and carbon atom 4 of the respective sugars. The α-form of the linkage between the sugars is preferred.

The linkage of A to Z takes place, for example, via one of the oxygen atoms of Z or via one of the carbon atoms of Z, preferably via the carbon atom of the $CH_2$ group of Z. The linkage of the radicals for A 10) to 12) preferably takes place via a carbon atom of Z, the other linkages of A preferably take place via an oxygen atom of Z.

The linkage of R to Z takes place analogously to the linkages of the di-, tri-, tetra-, penta- or hexasugars. Furthermore, the linkage from R to Z can also be replaced one or more times by —$CH_2$— or —S—.

If the sugar is substituted, the substitution preferably takes place on the hydrogen atom of an OH group of the sugars.

The term insulin-resistant tissue is understood as meaning, for example, rat fat cells which no longer contain any insulin receptor.

The compounds according to the invention can contain one or more phosphate groups which can also be additionally derivatized by a phosphate protective group. Phosphate protective groups are, for example, phenyl, benzyl or hydroxypropylnitrile (Houben Weyl, Methoden der Organischen Chemie [Methods of Organic Chemistry], Volume 12/1 or Volume 12/2; Teilheimer, Synthetic Methods of Organic Chemistry, Vol 45).

Physiologically tolerable salts of the compound of the formula I are in particular understood as meaning pharmaceutically utilizable or nontoxic salts. Such salts are formed, for example, from compounds of the formula I which contain acidic groups, e.g. phosphates or sulfates, with alkali metals or alkaline earth metals, such as, for example, Na, K, Mg and Ca, and also with physiologically tolerable organic amines, such as, for example, triethylamine and tris(2-hydroxyethyl)amine. Compounds of the formula I which contain basic groups, e.g. an amino group, form salts with inorganic acids, such as, for example, hydrochloric acid, sulfuric acid or phosphoric acid and with organic carboxylic or sulfonic acids, such as, for example, acetic acid, citric acid, benzoic acid, maleic acid, fumaric acid, tartaric acid and p-toluenesulfonic acid. Compounds in which basic and acidic groups are present in equal number form internal salts and are not dependent on a third salt component.

Methods of Synthesis

The invention furthermore relates to a process for the preparation of the compound of the formula I, which comprises synthesizing the inositolglycan stepwise from protected sugar and inositol precursors, then adding the radical A and removing from the compound obtained one or more protective groups introduced temporarily for the protection of other functions and converting the compound of the formula I thus obtained, if appropriate, into its physiologically tolerable salt.

The synthesis of the di- to polysugars is carried out by known processes (H. Paulsen, Angew. Chem. Int. Ed. 21 (1982) p. 155). The trichloroacetimidate method is preferably used for the synthesis of oligosaccharides (R. R. Schmidt, Angew. Chem. Int. Ed. 25 (1986) 212–235; T. Ogawa, Tetrahedron Lett. 31 (1990) 2439–2442).

The synthesis of the phosphates is carried out with the aid of the H-phosphate and the phosphoramidite method.(W. Bannwath et al., Helvetica Chemica Acta, 70 (1987), pages 175–186; L. A. Slotin, Synthesis (1977), pages 737–752)

The following are essentially possible protective groups for the hydroxyl groups of the sugars: benzyl, acetyl, benzoyl, pivaloyl, trityl, tert-butyidimethylsilyl, benzylidene, cyclohexylidene or isopropylidene protective groups.

Pharmaceutical Compositions

The compounds of the formula I and their physiologically tolerable salts are primarily used as active compounds for pharmaceutical preparations for the treatment of diabetes mellitus or noninsulin-dependent diabetes.

The invention therefore also relates to a pharmaceutical preparation which comprises at least one compound of the formula I and/or at least one of its physiologically tolerable salts in dissolved, amorphous and/or crystalline form— preferably in amorphous and/or crystalline form.

The pharmaceutical preparation is preferably a solution or suspension for injection having a pH of approximately 3.0 to 9.0, preferably of approximately 5.0 to 8.5, which contains a suitable isotonicizing agent, a suitable preservative and, if appropriate, a suitable buffer, and if appropriate also a depot principle, all in sterile aqueous solution or suspension. All of the preparation constituents apart from the active compound forms the preparation excipient. Suitable isotonicizing agents are, for example, glycerol, glucose, mannitol, NaCl, calcium or magnesium compounds such as, for example, $CaCl_2$ or $MgCl_2$. Suitable preservatives are, for example, phenol, m-cresol, benzyl alcohol and/or p-hydroxybenzoic acid esters.

Buffer substances which can be used, in particular for adjusting a pH of approximately 5.0 to 8.5, are, for example, sodium acetate, sodium citrate or sodium phosphate. Otherwise, physiologically acceptable dilute acids (typically HCl) or alkalis (typically NaOH) are also suitable for adjusting the pH.

For the purpose of varying the profile of action of the preparation according to the invention, modified (cf. EP-B 132 769 and EP-B 132 770) and/or unmodified insulins, preferably bovine, porcine or human insulin, in particular human insulin, can also be admixed.

The pharmaceutical preparation is prepared by bringing at least one compound of the formula I and/or at least one of its physiologically tolerable salts, if appropriate together with modified and/or unmodified insulin or insulin derivatives, into a suitable administration form using a physiologically acceptable excipient and also, if appropriate, using suitable additives and auxiliaries.

A typical pharmaceutical preparation will contain a unit dose of at least one compound according to formula I and/or at least one of its physiologically tolerable salts, optionally in combination with modified and/or unmodified insulin or insulin derivatives. A unit dose is an amount which either alone or in combination with other unit doses provides an efficacious amount of the active ingredient or ingredients. An efficacious amount is an amount sufficient to yield insulin-like activity.

Methods of Treatment

The pharmaceutical compositions comprising compounds of the formula I and their physiologically tolerable salts are primarily used as active compounds in the treatment of disorders characterized as treatable using compounds which exhibit insulin-like activity.

The invention therefore embodies methods of treatment which generally comprise administering to a patient in need of treatment and efficacious amount of at least one compound having insulin-like activity. Preferred compounds are described above according to formula I. The preferred compounds most often will be administered as a pharmaceutical formulation as described above. The patient may be a human or non-human animal.

A patient will be in need of treatment when suffering from a disorder which is treatable using insulin or compounds having insulin-like activity. Most typically, a patient will be in need of treatment when suffering from diabetes mellitus or noninsulin-dependent diabetes. The compound may be administered by any route, including subcutaneously, intradermally, intravenously, and preferably orally.

The amount administered will vary depending, among other things, upon the exact identity of the compound having insulin-like activity, the nature of the disorder being treated, specific patient characteristics and, most importantly, the judgement of the attending physician. The amount administered will generally be sufficient to observe efficacy. Such an amount would be considered an efficacious or therapeutically effective amount. Thus, an efficacious or therapeutically effective amount will normally be an amount sufficient to observe insulin-like activity. Of course, insulin-like activity can be assessed using methods well known in the medical arts. German Application No. 19649350.1, filed Nov. 28, 1996 is hereby specifically incorporated by reference in its entirety.

The invention is now explained in greater detail by means of the following non-limiting examples.

EXAMPLES

Example 1

Preparation of the compound B

This Example provides an exemplary synthesis which is useful in the preparation of compounds according to the invention.

The synthesis course can be inferred from the reaction scheme at the end of Example 1.

Synthesis of compound 3

60 g (94 mmol) of 1 (T. G. Mayer, B. Kratzer, R. R. Schmidt, Angew. Chem. 106 (1994) 2289–93) and 21.2 g (42.4 mmol) of 2 (A. Termin, R. R. Schmidt, Liebigs Ann. Chem. (1989) 789–795) are dissolved in 200 ml of dry methylene chloride and 400 ml of dry n-heptane. After addition of 70 g of dried molecular sieve (0.4 nm), the mixture is stirred at room temperature for 15 minutes. 5 ml of 0.05 M trimethylsilyltrifluormethane-sulfonic acid in methylene chloride (described as catalyst solution in the following procedures) are then added. After 15 minutes, 300 ml of n-heptane/ethyl acetate (1:1) are added and the mixture is filtered through silica gel. The silica gel is washed with n-heptane/ethyl acetate (1:1) and the filtrate is then concentrated. After purification by means of flash chromatography, 41.0 g (99%) of 3 are obtained as a colorless oil. TLC: n-heptane/ethyl acetate (1:1), $R_f$=0.6, MS: $(M+Li)^+$=981.1, calculated $C_{55}H_{67}N_3O_{11}Si$, M=974.21.

Synthesis of imidate 4

41 g (42.0 mmol) of 3 are dissolved in 400 ml of tetrahydrofuran (THF) and 9 ml of acetic acid. After addition of 70 ml of 1 M TBAF/THF solution, the mixture is allowed to stand at room temperature for 8 hours. The acetic acid is removed by freezing (16 h at −30° C.) and the filtrate is purified by means of flash chromatography after concentration. Yield 34.1 g (94%) of deprotected compound. This is dissolved in 300 ml of dry methylene chloride. After addition of 50 ml of trichloroacetonitrile and 20 g of potassium carbonate, the mixture is stirred at room temperature for 4 hours. It is filtered through silica gel, the silica gel is washed with n-heptane/ethyl acetate (1:1) and the filtrate is concentrated. Crude yield: 42.1 g. TLC: n-heptane/ethyl acetate (2:1), $R_f$=0.5. $^1$H- NMR (CDCl$_3$): characteristic signals for imidate; σ=8,78, for NH and 5.63 for the anomer (β-imidate).

Synthesis of trisaccharide 6

33.2 g (33.0 mmol) of 4 and 13.3 g (25.0 mmol) of 5 (R. Aneja, S. G. Aneja, A. Parra, Tetrahedron, Asymmetry 6 (1995) 17–18; C. J. J. Elie, R. Verduyn, C. E. Dreef, D. M. Braunts, G. A. van der Marel, J. H van Boom, Tetrahedron, 46 (1990) 8243–54) are dissolved in 120 ml of dry methylene chloride and 360 ml of dry n-heptane. After addition of 100 g of molecular sieve, the mixture is stirred at room temperature for 15 minutes. It is cooled to −20° C. under argon and then treated with 20 ml of catalyst solution. After 30 minutes, the mixture is allowed to thaw to room temperature. For working up, it is filtered through silica gel and the silica gel is washed with n-heptane/ethyl acetate (1:1). The filtrate is concentrated and the crude product (46.2 g) is dissolved in 150 ml of methylene chloride. After addition of 400 ml of methanol and 15 ml of 1 M NaOMe/MeOH solution, the mixture is allowed to stand at room temperature for 16 hours. The solution is treated with 1 ml of water and concentrated. The oil obtained is dissolved in 50 ml of ethyl acetate, diluted with 200 ml of n-heptanelethyl acetate (1:1)

and filtered through silica gel. After concentration, the residue is purified by flash chromatography. Yield 32.5 g (97%) of white foam as an anomer mixture. TLC: n-heptane/ethyl acetate (2:1), $R_f$=0.5. MS: $(M+Li)^+$=1336.7; calculated $C_{80}H_{87}N_3O_{15}$, M=1330.59.

Synthesis of trisaccharide 7

The anomer mixture 6 can only be easily separated chromatographically as the derivative 7.32.4 g (24.4 mmol), of 6 are dissolved in 200 ml of methylene chloride. After addition of 500 ml of 0.5 M HCl/MeOH (from 17.5 ml of AcCl in 500 ml of MeOH) and 20 ml of ethylene glycol, the mixture is allowed to stand at room temperature for 17 hours. After concentration, the residue is purified by flash chromatography. The product obtained (26.9 g, 88%) is dissolved in 300 ml of methylene chloride. 3.0 g of imidazole and 4.6 g of TBDMSCl are added. After 16 hours at room temperature, the mixture is diluted with 500 ml of n-heptane/ethyl acetate (2:1) and filtered through silica gel. The silica gel is washed with n-heptane/ethyl acetate (2:1) and the filtrate is concentrated. The crude product obtained is purified by flash chromatography. Yield 21.1 g (72%) of 7 and 6.3 g (22%) of alpha product. TLC: n-heptane/ethyl acetate (2:1), $R_f$=0.5 for 7 and $R_f$=0.3 for the alpha product. MS: $(M+Li)^+$=1370.6; calculated $C_{80}H_{93}N_3O_{15}Si$, M=1364.71.

Synthesis of trisaccharide 8

21.2 g (15.5 mmol) of 7 are dissolved in 60 ml of methylene chloride and 180 ml of dimethoxypropane. 250 mg of TsOH are added and the mixture is allowed to stand at room temperature for 1 hour. After addition of 2 ml of trimethylamine, it is concentrated and 23.1 g of crude product are obtained. This is dissolved in 150 ml of THF and treated with 30 ml of 1 M TBAF/THF solution. After 16 hours, it is concentrated and purified by flash chromatography. Yield: 20.0 g (99%) of 8 as a white foam. TLC: n-heptane/ethyl acetate (2:1), $R_f$=0.4. MS: $(M+Li)^+$=1296.7; calculated $C_{77}H_{83}N_3O_{15}$, M=1290.51.

Synthesis of tetrasaccharide 10

20.0 g (15.4 mmol) of 8 and 15.0 g (23.5 mmol) of 9 (T. G. Mayer, B. Kratzer, R. R. Schmidt, Angew. Chem. 106 (1994) 2289–93) are reacted analogously to the procedure for compound 6 and 20.3 g (76%) of tetrasaccharide 10 are obtained as a white foam. TLC: n-heptane/ethyl acetate (2:1), $R_f$=0,6, MS: $(M+Li)^+$=1770, calculated $C_{107}H_{115}N_3O_{20}$, M=1763.09.

Synthesis of pentasaccharide 12

20.3 g (11.8 mmol) of 10 and 12.0 g (20.3 mmol) of 11(T. G. Mayer, B. Kratzer, R. R. Schmidt, Angew. Chem. 106 (1994) 2289–93) are reacted analogously to the procedure for compound 6 and 19.4 g (80%) of deacylated product are obtained. This product is dissolved in 200 ml of methylene chloride and treated with 3.4 g (50.0 mmol) of imidazole. 6.0 g (40.0 mmol) of TBDMSCl are added and the mixture is stirred at room temperature for 15 hours. After addition of 5 ml of methanol, it is allowed to stand for 10 minutes, then diluted with 200 ml of n-heptanelethyl acetate (1:1) and filtered through silica gel. The silica gel is additionally washed with 200 ml of n-heptanelethyl acetate (1:1), and the filtrate is concentrated and purified by means of flash chromatography. Yield: 19.4 g (95%) of 12 as a white foam. TLC: n-heptane/ethyl acetate (2:1), $R_f$=0,7. MS: $(M+Li)^+$= 2226; calculated $C_{133}H_{151}N_3O_{25}Si$, M=2219.75

Synthesis of hexasaccharide 14

19.4 g (8.9 mmol) of 12 and 14.0 g (20.,0 mmol) of 13 (T. G. Mayer, B. Kratzer, R. R. Schmidt, Angew. Chem. 106 (1994) 2289–93) are dissolved in 100 ml of dry methylene chloride and 300 ml of dry n-heptane. After addition of 40 g of molecular sieve (0.4 nm), the mixture is stirred at room temperature for 15 minutes. 10 ml of catalyst solution are added and the mixture is stirred for a further 15 minutes. For working up, it is filtered through silica gel and the silica gel is washed with n-heptane/ethyl acetate (1:1). The filtrate is concentrated and 33 g of crude product are obtained. This is dissolved in 200 ml of methylene chloride and treated with 500 ml of 0.5 M HCl in methanol. After two hours at room temperature, the mixture is concentrated and concentrated several times with methylene chloride. The intermediate obtained is dissolved in 200 ml of methylene chloride and treated with 3.4 g (50 mmol) of imidazole and 6.0 g of (40 mmol) of TBDMSCl. After 16 hours (h), the mixture is worked up analogously to compound 12, Yield 20.2 g (85%) of 14 as a white foam. TLC: n-heptane/ethyl acetate (2:1), $R_f$=0,3. MS: $(M+Li)^+$=2669; calculated $C_{161}H_{177}N_3O_{30}Si$, M=2662.26

Synthesis of compound 15

30.0 g of triazole are dissolved in 800 ml of dry THF. 13.5 ml of phosphorus oxychloride are added dropwise at 10° C. 60 ml of triethylamine are then added dropwise and the mixture is stirred at room temperature for 15 minutes. The precipitate is filtered and washed with a little dry THF. The filtrate is added to 19.1 g (7.2 mmol) of 14. The solution is concentrated to 100 ml. After 15 minutes, it is diluted with 500 ml of ethyl acetate and washed twice with 100 ml of water. The organic phase is dried over magnesium sulfate, filtered and concentrated. After flash chromatography, 19.0 g (97%) of cyclic phosphate derivative are obtained as a white foam. TLC: methylene chloride/methanol/33% $NH_3$ (100/7/1), $R_f$=0.3. MS: $(M+2Li-H)^+$=2737; calculated $C_{161}H_{174}N_3O_{32}PSi$, M=2724.22. The cyclic phosphate is dissolved in 350 ml of THF and 100 ml of TBAF (1M in THF) are added. After 20 hours, the mixture is concentrated and the residue is purified by flash chromatography. Yield 18.1 g (99%) of 15 as a white foam. TLC: methylene chloridelmethanol/33% $NH_3$ (100/7/1), $R_f$=0,3 (runs identically to the starting material) MS: $(M+2Li-H)^+$=2622; calculated $C_{155}H_{162}N_3O_{32}P$, M=2609.96.

Synthesis of compound 16

14 g of phosphorous acid is concentrated four times with pyridine and then taken up in 200 ml of dry pyridine. 16 ml of pivaloyl chloride are added dropwise at 10° C. This reaction solution is allowed to stand at room temperature for 15 minutes. 18.1 g (6.9 mmol) of 15 are introduced into the reaction solution described above. After 1 hour, it is diluted with 200 ml of toluene and 150 ml of methylene chloride/methanol/33% $NH_3$ (30/10/3). After concentrating, residual pyridine is distilled out a further three times with toluene. The residue is suspended in 200 ml of methylene chloride/methanol (20:1). The nonsoluble constituents are filtered and washed twice with 50 ml of methylene chloride/methanol (20:1). The filtrate is concentrated and purified by flash chromatography. Yield 16.9 g (91%) of protected final product. TLC: methylene chloride/methanol/33% $NH_3$ (100/7/1), $R_f$=0.25.

MS: $(M+3Li-2H)^+$=2691; calculated $C_{155}H_{163}N_3O_{34}P_2$, M=2673,94. For deprotection, 600 ml of ammonia are condensed at −78° C. 4.7 g (204 mmol) of sodium are dissolved therein. This solution is diluted with 300 ml of dry THF and 16.9 g (6.3 mmol) of protected final product dissolved in 100 ml of dry THF are then slowly added dropwise at a reaction temperature of −78° C. After a reaction time of 15 minutes (blue color must not disappear), the mixture is treated cautiously with 10 g of ammonium chloride. When the blue color has disappeared, the mixture is diluted cautiously with 100 ml of water and 300 ml of methanol. It is allowed to thaw and then concentrated to around 150 ml. This solution is diluted with 2 l of methylene chloride/methanol/33% NH$_3$ (3/3/1) and added to a flash silica gel column (700 ml of silica gel). It is eluted with 3 l of methylene chloride/methanol/33% NH$_3$ (3/3/2) and then with 3 l (3/3.5/3). The product elutes if the mixture is then chromatographed using n-butanol/ethanol/water/33% NH$_3$ (2/2/2/1). Yield 5.5 g (78%) of 16 as a white solid. TLC: (2/2/2/1), R$_f$=0,4. MS: (M+H)$^+$=1116,5; calculated C$_{36}$H$_{63}$NO$_{34}$P$_2$, M=1115,83. $^{31}$P-NMR (D$_2$O) σ=16,3 ppm for cyclic phosphate and 7.9 for H-phosphate.

The compounds A, C, D, E, F, G, H, I and J–W (table 2) are prepared analogously to the methods according to Example 1. Table 1 shows the structural formulae, empirical formula and mass spectrum of the compounds A, C, D, E, F, G, H and I. The mass spectra of compounds J–W are in accordance with the calculated theoretical values.

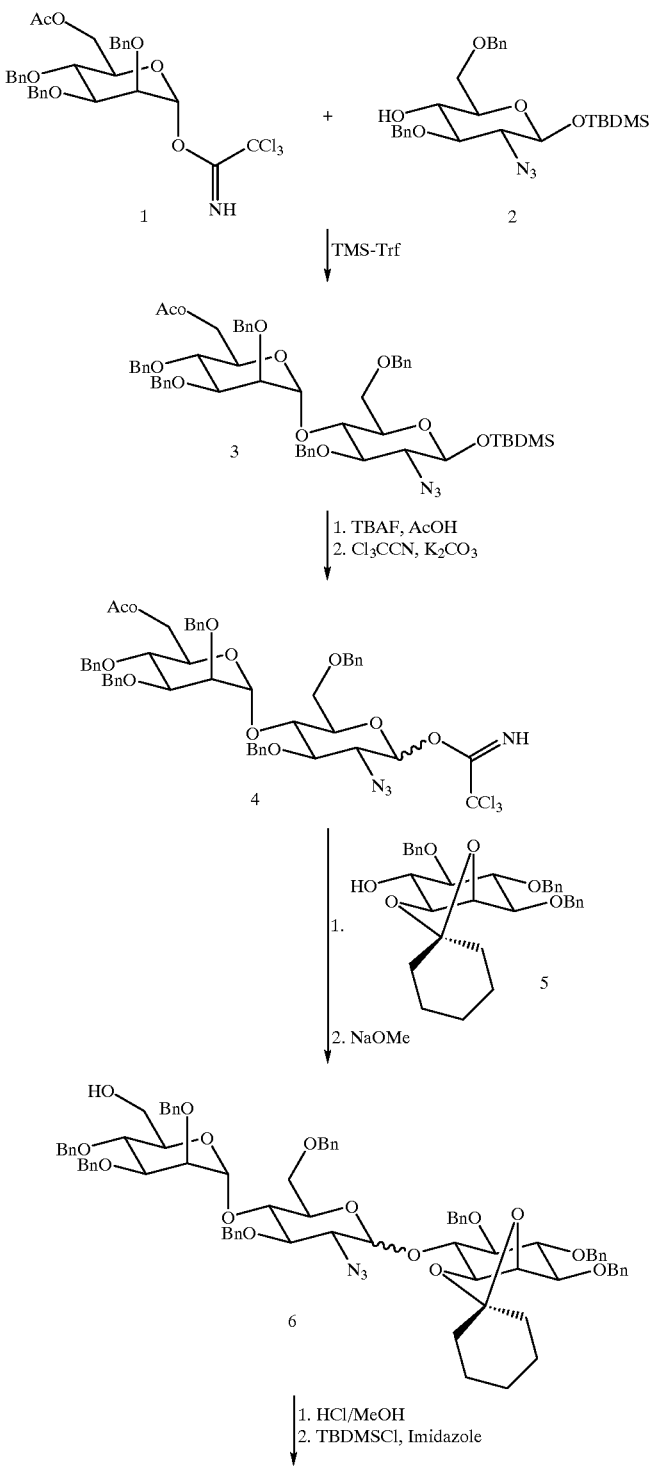

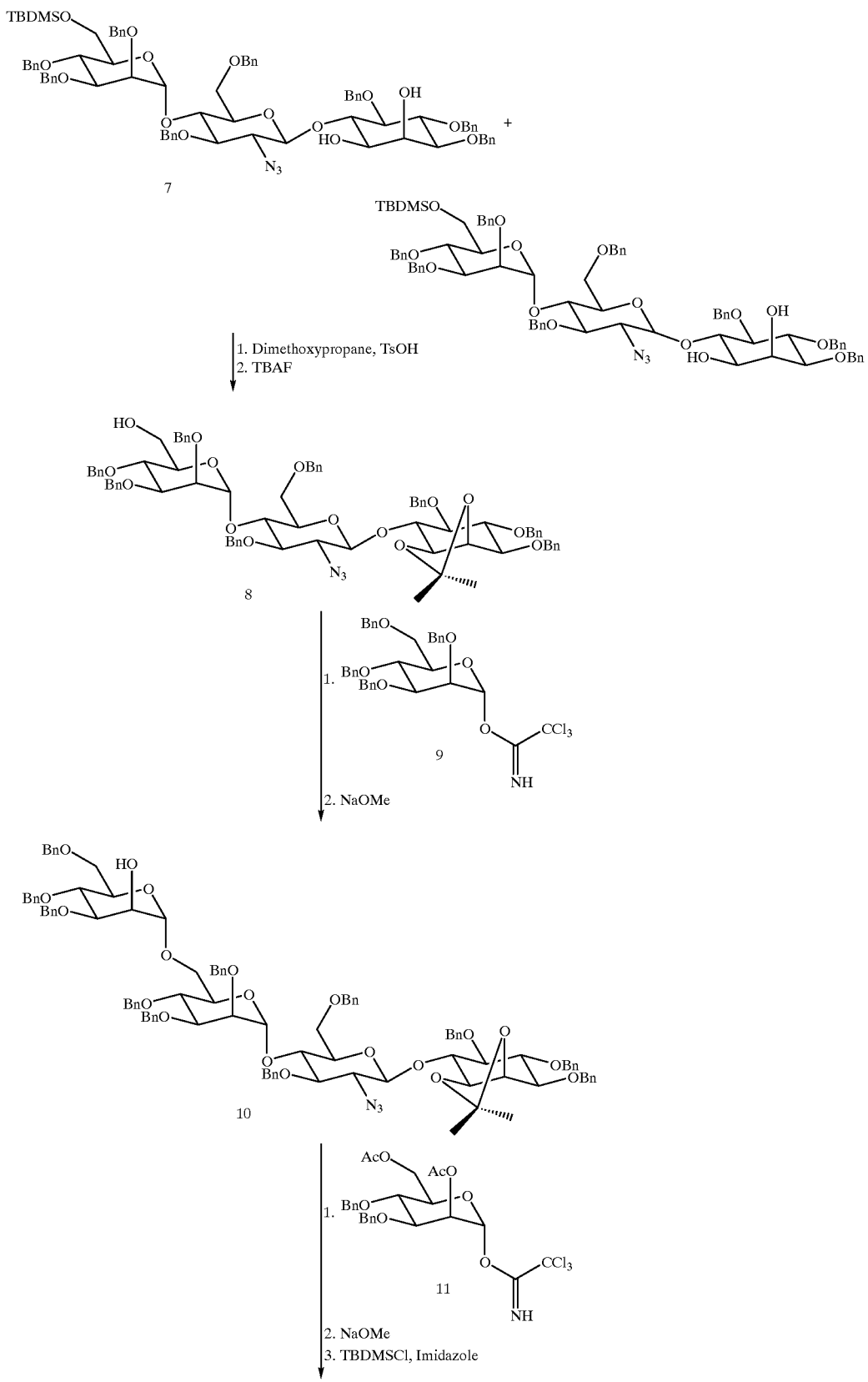

-continued
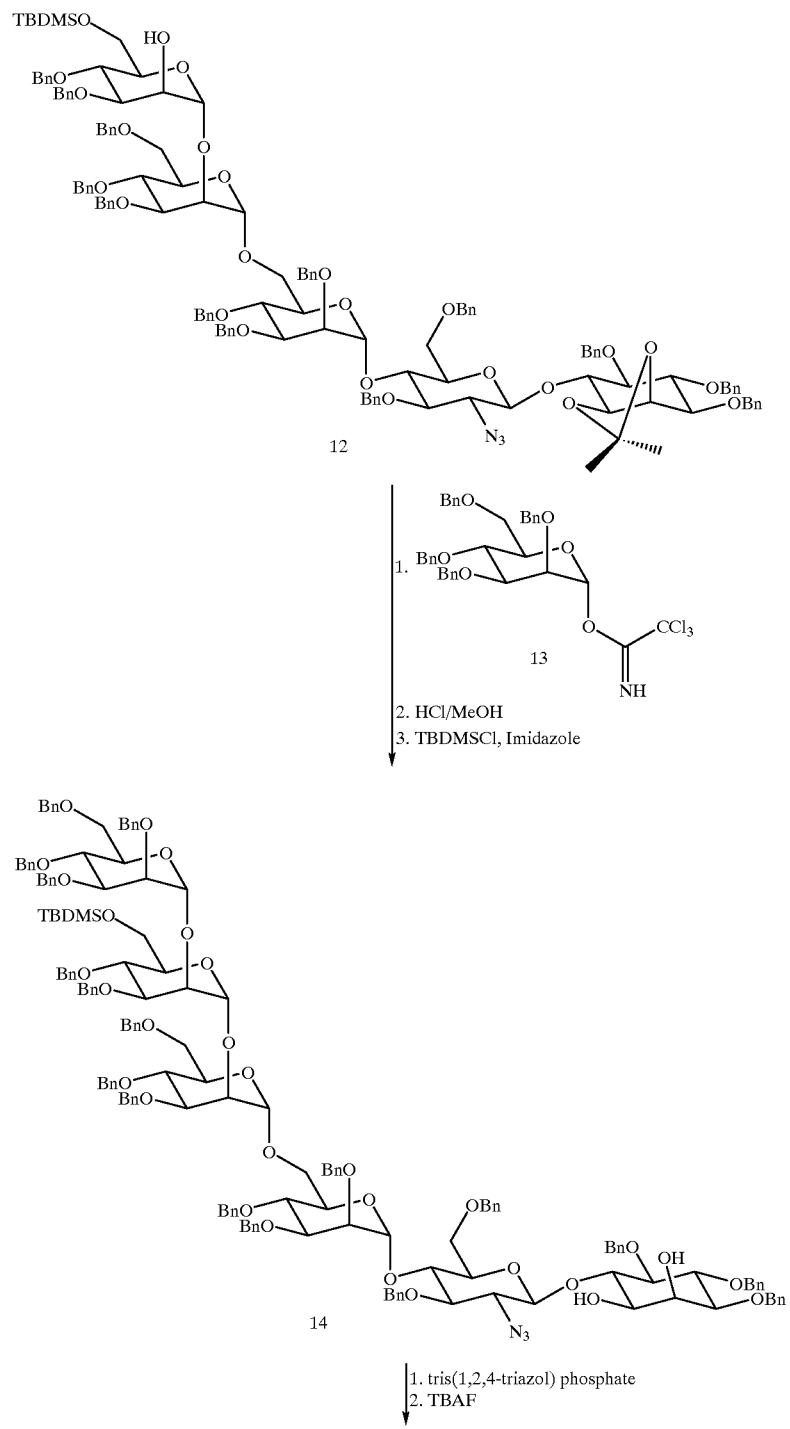

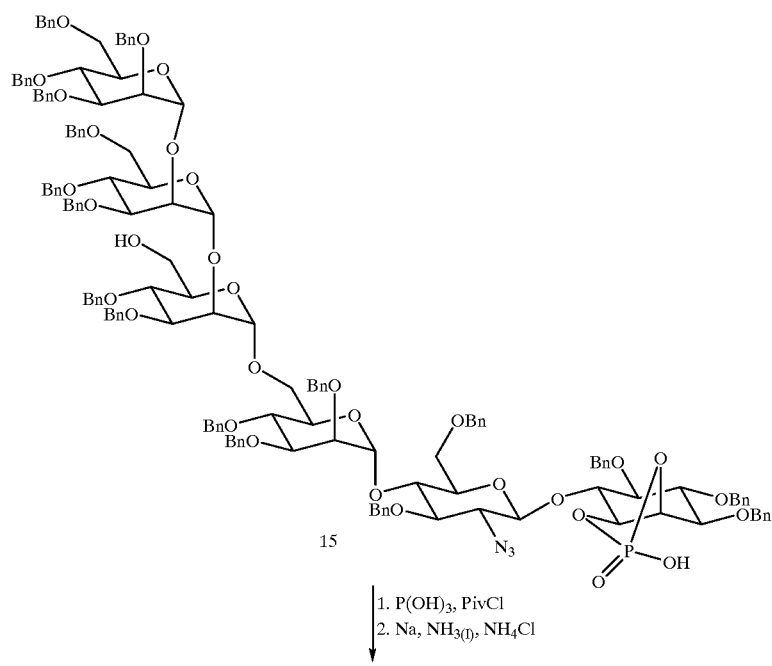
1. P(OH)₃, PivCl
2. Na, NH₃₍ₗ₎, NH₄Cl
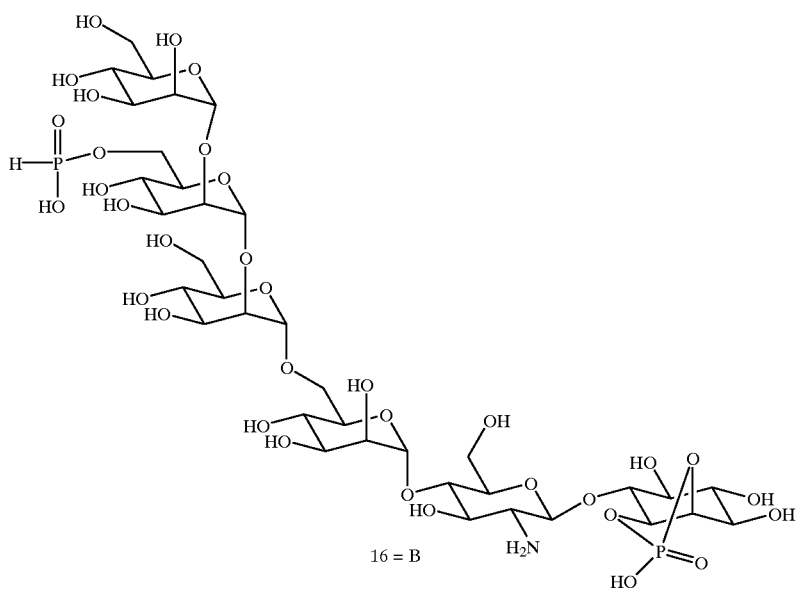
16 = B

TABLE 1
| Compound | Sumformula | Mass spectrum $(M + H)^+$ |
|---|---|---|
| A 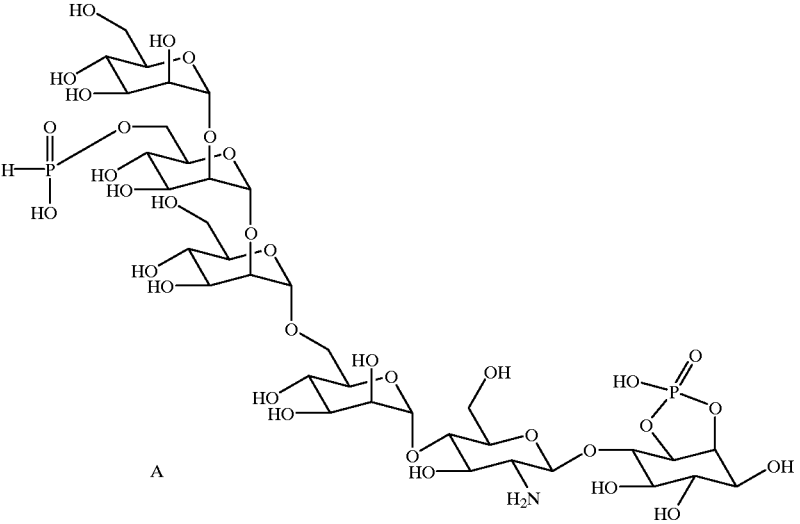 | $C_{36}H_{63}NO_{34}P_2$ | 1116.5 |
| B 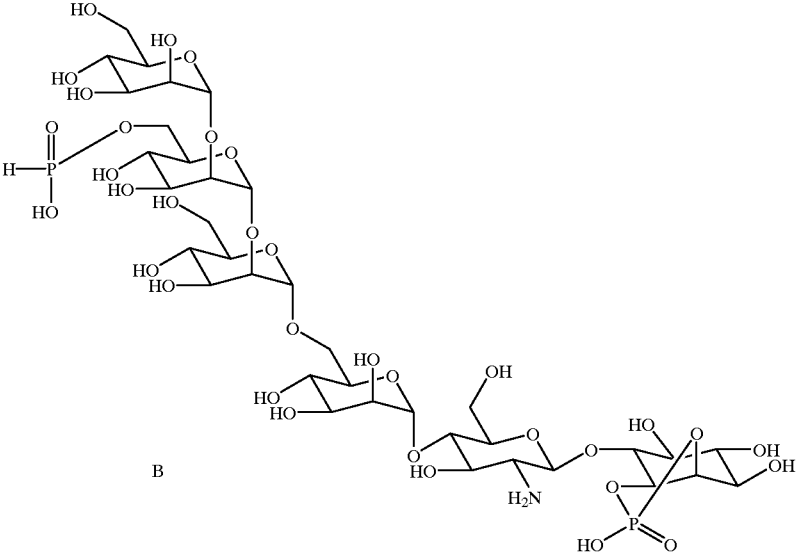 | $C_{36}H_{63}NO_{34}P_2$ | 1116.5 |

TABLE 1-continued

| Compound | Sumformula | Mass spectrum (M + H)+ |
|---|---|---|
| C | $C_{36}H_{63}NO_{33}P_2S$ | 1132.7 |
| D | $C_{36}H_{65}NO_{35}P_2$ | 1134.4 |

TABLE 1-continued

| Compound | Sumformula | Mass spectrum (M + H)+ |
|---|---|---|
| E | $C_{40}H_{75}N_3O_{40}P_4$ | 1362.8 |
| F | $C_{36}H_{65}NO_{35}P_2$ | 1134.4 |
| G | $C_{18}H_{33}NO_{19}P_2$ | 630.3 |

TABLE 1-continued

| Compound | Sumformula | Mass spectrum (M + H)+ |
|---|---|---|
| H (structure) | $C_{18}H_{34}NO_{17}P$ | 568.2 |
| I (structure) | | (M + H) 1334.6 |

Example 3
Pharmaceutical activity

This example provides exemplary methods for determining insulin-like activity. The biological activity of the compounds of the formula I according to the invention is determined with the aid of isolated fat cells from the rat.

The preparation of fat cells from the rat was carried out as follows: White fatty tissue of the epididymis (Wistar rat, 160–180 g, no food restriction) is digested with collagenase and the resulting isolated fat cells are separated off by means of filtration of undigested tissue and washed by flotation several times using Krebs-Ringer-Henseleit buffer (KRH buffer).

A) Lipogenesis

This test determines the insulin-stimulable conversion of glucose into toluene-soluble products (triglycerides, phospholipids, fatty acids), which promotes glucose transport and triglyceride (glycerol-3-P synthesis, esterification)/phospholipid/fatty acid synthesis including the insulin signal transmission cascade. At a glucose concentration of 2.5 mM in the test, the esterification (and not the glycerol-3-P synthesis including glucose transport) is rate-determining for the stimulation of lipogenesis.

200 µl ($3\times10^5$ cells/ml) of rat fat cells in KRH buffer are incubated at 37° C. for 90 min with 100 µl of D-[3-$^3$H] glucose (25 mM, 0.4 µCi) in the presence or absence of insulin (10 ng/ml) or compound of the formula I according to the invention (final volume 1 ml). By addition of a toluene-soluble scintillation cocktail (10 ml), the cells are disrupted and the lipids are separated off from water-soluble products and the incubation medium. After phase separation, the radioactivity incorporated in lipid products is determined directly without removal of the aqueous phase by scintillation measurement ([$^3$H]lipid [dpm$\times10^{-3}$]). A control value (incubation under identical conditions but without cells) is subtracted from this radioactivity. The lipogenesis rate is linear up to 120 min. The maximum stimulation factor—this is the ratio of the incubation result with insulin to the incubation results without insulin—is set at 100%. The percentage data under "%Ins$_{max}$" are parts of the maximum stimulation factor defined in this way. The term EC$_{50}$ indicates the concentration of the compound of the formula I at which 50% of the maximum stimulation to be achieved by the respective compound of the formula I is to be observed.

B) Glucose transport

Rat fat cells in 100 µl of KRH buffer (titer $5\times10^5$ cells/ml) are incubated with gentle shaking at 37° C. for 15 min with insulin or with the compound of the formula I according to the invention. After addition of 15 µl of 2-[$^3$H]- at room temperature. After specified times (0–20 min), 100 μl of the test batch are removed and transferred to a reaction vessel (contents 400 μl), in which 250 μl of dinonyl phthalate have been initially introduced. After centrifugation (15,000×g, 1 min), the cells are separated off from the oily layer of the incubation medium underneath the oily layer by cutting the tube at the level of the oily layer and transferring to a scintillation vessel. After addition of 5 ml of water-soluble scintillation fluid, the radioactivity is determined. This total cell-associated radioactivity is corrected for [$^3$H]-deoxyglucose which has passively diffused into the cells and is included in the cell interstices by subtraction of a control value (incubation in the presence of the glucose transport inhibitor cytochalasin B). The initial (stimulated) glucose transport rate is linear up to 15 min. The maximum stimulation factor—this is the ratio of the incubation result with insulin to the incubation result without insulin—is set at 100%.

The terms "%Ins$_{max}$" and "EC$_{50}$" are as defined under A) lipogenesis.

What is claimed is:

1. A compound of the formula I:

A—Z—R            (I)

any physiologically tolerable salt thereof and any stereoisomeric form, wherein:

A is a radical selected from the group consisting of H—P(O)(OH)—, H—P(S)(OH)—, HO—P(S)(OH)—, HS—P(S)(OH)—, (C$_1$–C$_4$)-alkyl-P(O)(OH)—, (C$_1$–C$_4$)-alkyl-P(S)(OH)—, S(O)$_2$(OR$^1$)—, S(O)(OR$^1$)—, NH$_2$—C(O)—, R$^1$R$^2$N—, R$^1$R$^2$N—C(O)—NH—, R$^1$O—SO$_2$—NH—, (C$_1$–C$_4$)-alkyl-SO$_2$—, (C$_1$–C$_4$)-alkyl-S(O)—, and R$^1$—S—, in which R$^1$ and R$^2$ independently of one another are hydrogen or (C$_1$–C$_4$)-alkyl;

Z is either (a) 2 to 6 sugar radicals or (b) 2 to 6 sugar radicals, mono- to hexasubstituted independently of one another by a radical selected from the group consisting of: methyl; sugar radical; disugar radical; —SO$_2$—OH; —C(O)—NR$^1$R$^2$; —C(O)—(C$_1$–C$_4$)-alkyl; —P(O)(H)OH; —P(O)(OH)$_2$; —P(S)(H)OH;

TABLE 2

| | | Lipogenesis | | Glucose transport | |
|---|---|---|---|---|---|
| Formulae | Compound | % Ins$_{max}$ | EC$_{50}$[μM] | % Ins$_{max}$ | EC$_{50}$[μM] |
| HO-PO(H)O-6Manα1(Manα1-2)-2Manα1-6Manα1-4GluNβ1-6(L)inositol-1,2-(cyclic)-phosphate | A | 59 | 7 | 28 | 8 |
| HO-PO(H)O-6Manα1(Manα1-2)-2Manα1-6Manα1-4GluNβ1-6(D)inositol-1,2-(cyclic)-phosphate | B | 77 | 8,2 | 41 | 8,1 |
| HO-PO(H)O-6Manα1(Manα1-2)-2Manα1-6Manα1-4GluNβ1-6(D)inositol-1,2-(cyclic)-thiophosphate | C | 64 | 7 | 29 | 10 |
| HO-PO(H)O-6Manα1(Manα1-2)-2Manα1-6Manα1-3GluNβ1-6(L)inositol-3-phosphate | D | 33 | 20 | 18 | 18 |
| HO-PO(H)O-6Manα1(Manα1-2)-2Manα1(6-EtNP)-6Manα1(2-EtNP)-4GluNβ1-6(D)inositol-1,2-(cyclic)-phosphate | E | 48 | 60 | 34 | 30 |
| HO-PO(H)O-6Manα1(Manα1-2)-2Manα1-6Manα1-4GluNα1-6(L)inositol-2-phosphate | F | 53 | 15 | 26 | 25 |
| HO-PO(H)O-6Manα1-4GluNα1-6(L)inositol-1,2-(cyclic)-phosphate | G | 25 | 15 | 9 | 15 |
| HO-PO(H)O-6Manα1-4GluNα1-6(L)inositol | H | 15 | 25 | 2 | 10 |
| HO-PO(H)O-6Manα1-6-Manα1-6Manα1-6Manα1-3GluNβ1-6(L)inositol-3-phosphate | I | 18 | 20 | 14 | 50 |
| HO-PO(H)O-6Manα1(Manα1-2)-2-Manα1-6-Manα1-4GluN(HSO$_3$)β-1-6(L)-inositol-1,2-(cyclic)-phosphate | J | 63 | 8 | 21 | 3 |
| H$_2$N-CO-6Manα1(Manα1-2)-2Manα1-6Manα1-4GluNβ1-6(D)-inositol-1,2-(cyclic)-phosphate | K | 72 | 8 | 23 | 15 |
| HO-SO$_2$-6Manα1(Manα1-2)-2Manα1-6Manα1-4GluNβ1-6(D)-inositol-1,2-(cyclic)-phosphate | L | 84 | 7 | 36 | 8 |
| HO-PO(H)O-6Manα1(Manα1-2)-2Manα1(6-PO(H)OH)-6Manα1-4GluNβ1-6(D)-inositol-1,2-(cyclic)-phosphate | M | 90 | 7 | 39 | 6 |
| HO-SO$_2$-O-6Manα1(Manα1-2)-2Manα1(6-HSO$_3$)-6Manα1-4-GluNβ1-6(D)-inositol-1,2-(cyclic)-phosphate | N | 96 | 3 | 52 | 5 |
| HO-PO(H)O-6-Manα1-6Manα1-6Manα-1-6Manα1-6Manα1-6(L)inositol-3-phosphate | O | 10 | 20 | 5 | 50 |
| HO-PO(H)O-6-Manα1(Manα1-2)-2-Manα1-6Manα-3GluNβ1-6(L)-inositol-3-phosphate | P | 32 | 20 | 18 | 20 |
| HO-PO(H)O-6Manα1-2Manα1(6-PO(H)OH)-6-Manα1-3GluNβ1-6(L)inositol-3-phosphate | Q | 44 | 40 | 18 | 30 |
| H$_2$N-CO-O-6Manα1(Manα1-2)-2Manα1(6-CO-NH$_2$)-6Manα1-3GluNβ1-6(L)inositol-3-phosphate | R | 48 | 15 | 19 | 10 |
| Manα1-2Manα1-2Manα1(6-HSO$_3$)-6Manα1-6Manα1-6(D,L)inositol-3-phosphate | S | 50 | 15 | 34 | 20 |
| HO-PO(H)O-6Manα1(Manα1-2)-2Manα1(6-PO(H)OH)-6Manα1-3GluNβ1-6(L)inositol-3-phosphate | T | 72 | 12 | 30 | 10 |
| Manα1-2Manα1-2Manα1(6-PO(H)OH)-6Manα1-3GluNβ1-6(L)inositol-3-phosphate | U | 80 | 15 | 34 | 15 |
| Manα1(Manα1-2)-2Manα1(6-HSO$_3$)-6Manα1-3GluNβ1-6(L)inositol-3-phosphate | V | 83 | 15 | 48 | 15 |
| HO-SO$_2$-O-6Manα1(Manα1-2)-2-Manα1(6-HSO$_3$)-6Manα1-3GluNβ1-6(L)inositol-3-phosphate | W | 86 | 10 | 42 | 10 |

—P(S)(OH)$_2$; —P(S)(SH)(OH); and —P(O)(OH)—O—CH$_2$—CH$_2$—NR$^1$R$^2$, and wherein the glycosidic bond between the 2 to 6 sugar radicals optionally is replaced one to six times by —CH$_2$— or —S—, and in which R$^1$ and R$^2$ independently of one another are a hydrogen atom or (C$_1$–C$_4$)-alkyl; and R is selected from the group consisting of inositol, inositol phosphate, inositol thiophosphate, inositol cyclophosphate, and inositol cyclothiophosphate, wherein the R moiety is optionally substituted as follows:

inositol phosphate, inositol thiophosphate, inositol cyclophosphate, and inositol cyclothiophosphate optionally are mono- or disubstituted, independently of one another, by phosphate or thiophosphate;

inositol phosphate, inositol thiophosphate, inositol cyclophosphate, and inositol cyclothiophosphate optionally are monosubstituted by either a cyclophosphate radical or a cyclothiophosphate radical;

and inositoll optionally has two adjacent OH groups and substituents selected from the group consisting of —CH$_2$, —SO$_2$ and —NH—.

2. A compound according to claim 1, wherein:

A is selected from the group consisting of H—P(O)(OH)—, S(O)$_2$(OR$^1$)— and NH$_2$—C(O)—;

Z is 2 to 6 sugar radicals selected from the group consisting of mannose, glucose, gluconic acid, galactonic acid, mannonic acid, glucosamine, fructose and galactose, wherein said 2 to 6 sugar radicals optionally are mono- to hexasubstituted independently of one another by a member selected from the group consisting of methyl, mannose, glucosamine, dimannose and mannose-glucosamine wherein the glycosidic bond of the two sugars mannose and glucosamine is between the carbon atoms 1–3, 1–2 or 1–6 of the two sugars; and R is selected from the group consisting of inositol, inositol phosphate, inositol thiophosphate, inositol cyclothiophosphate and inositol cyclophosphate.

3. A compound according to claim 1, wherein:

A is H—P(O)(OH)—;

Z is 2 to 4 sugar radicals selected from the group consisting of mannose, glucosamine and glucosamine which is monosubstituted by mannose; and R is selected from the group consisting of inositol, inositol phosphate and inositol cyclophosphate.

4. A process for preparing a compound according to claim 1, comprising synthesizing the inositolglycan stepwise from protected sugar and inositol precursors, then adding the radical A and removing from the compound obtained one or more protective groups introduced temporarily for the protection of other functions and optionally converting the compound of the formula I thus obtained into its physiologically tolerable salt.

5. A pharmaceutical preparation, comprising an efficacious amount of at least one compound according to claim 1 and a physiologically acceptable excipient.

6. A pharmaceutical preparation according to claim 5, further comprising at least one member of the group consisting of human, bovine or porcine.

7. A process for the production of a pharmaceutical preparation according to claim 5, comprising admixing at least one compound of the formula I into a suitable administration form using a physiologically acceptable excipient and optionally, suitable additives and/or auxiliaries.

8. The process as claimed in claim 7, further comprising adding at least one member of the group consisting of human, bovine and porcine insulin.

9. A method of treating diabetes, comprising administering to a patient in need of said treatment an efficacious amount of a compound according to claim 1.

10. A method according to claim 9, wherein said patient is suffering from diabetes mellitus or noninsulin-dependent diabetes.

* * * * *